US012808832B2

(12) United States Patent
Wu et al.

(10) Patent No.: US 12,808,832 B2
(45) Date of Patent: Nov. 24, 2026

(54) METHOD FOR PRODUCING ELECTROCHEMILUMINESCENCE NANOPROBE, ELECTROCHEMILUMINESCENCE NANOPROBE, ELECTROCHEMILUMINESCENCE SENSOR, ELECTROCHEMILUMINESCENCE DETECTION METHOD, AND KIT FOR ELECTROCHEMILUMINESCENCE DETECTION

(71) Applicants: CANON KABUSHIKI KAISHA, Tokyo (JP); Nanjing University, Nanjing (CN)

(72) Inventors: Xiaotian Wu, Beijing (CN); Qiqi Xu, Beijing (CN); Hao Huang, Beijing (CN); Huangxian Ju, Nanjing (CN); Jie Wu, Beijing (CN)

(73) Assignees: CANON KABUSHIKI KAISHA, Tokyo (JP); Nanjing University, Nanjing (CN)

( * ) Notice: Subject to any disclaimer, the term of this patent is extended or adjusted under 35 U.S.C. 154(b) by 92 days.

(21) Appl. No.: 18/738,839

(22) Filed: Jun. 10, 2024

(65) Prior Publication Data

US 2025/0003917 A1 Jan. 2, 2025

(30) Foreign Application Priority Data

Jun. 9, 2023 (CN) ......................... 202310685007.0

(51) Int. Cl.

| | |
|---|---|
| ***G01N 27/30*** | (2006.01) |
| ***C12Q 1/6825*** | (2018.01) |
| ***C12Q 1/70*** | (2006.01) |
| ***G01N 27/327*** | (2006.01) |

(52) U.S. Cl.

CPC ......... *G01N 27/305* (2013.01); *C12Q 1/6825* (2013.01); *C12Q 1/708* (2013.01); *G01N 27/3271* (2013.01); *G01N 27/3276* (2013.01)

(58) Field of Classification Search

CPC .... C12Q 1/6816; C12Q 1/6825; C12Q 1/708; C09K 2211/1416; C09K 2211/1425; C09K 2211/1483; C09K 2211/025; C09K 2211/06; G01N 27/305; G01N 27/3271; G01N 27/3276; G01N 27/76

See application file for complete search history.

(56) References Cited

PUBLICATIONS

Anal. Chem. 2021, 93, 5327-5333 (Year: 2021).*
Anal. Chem. 2021,93, 6857-6864 (Year: 2021).*
ACS Sens. 2020,970-977 (Year: 2020).*
ACS Appl. Mater. Interfaces 2019, 11, 27363-27370 (Year: 2019).*
(Continued)

*Primary Examiner* — Gurpreet Kaur

(74) *Attorney, Agent, or Firm* — Oblon, McClelland, Maier & Neustadt, L.L.P.

(57) ABSTRACT

A method for producing an electrochemiluminescence nanoprobe according to an embodiment includes: a Pdots nanoparticle synthesis step of synthesizing a Pdots nanoparticle by polymerizing a conjugated polymer and a copolymer molecule; and a Pdots nanoparticle modification step of modifying a resulting Pdots nanoparticle using an oligonucleotide chain modified with a quencher molecule.

20 Claims, 6 Drawing Sheets

Specification includes a Sequence Listing.

(56) References Cited

PUBLICATIONS

Wang, Ningning et al., "Electrochemiluminescent Imaging for Multi-immunoassay Sensitized by Dual DNA Amplification of Polymer Dot Signal", Analytical Chemistry, vol. 90, 2018, pp. 7708-7714.
Li, Guangming et al., "Ratiometric fluorescent detection of miRNA-21 via pH-regulated adsorption of DNA on polymer dots and exonuclease III-assisted amplification", Analytica Chimica Acta, vol. 1232, 340450, 2022, 8 pages.
Liu, Peng-Fei et al., "Cas12a-based electrochemiluminescence biosensor for target amplification-free DNA detection", Biosensors and Bioelectronics, vol. 176, 112954, 2021, 7 pages.

* cited by examiner

METHOD FOR PRODUCING ELECTROCHEMILUMINESCENCE NANOPROBE, ELECTROCHEMILUMINESCENCE NANOPROBE, ELECTROCHEMILUMINESCENCE SENSOR, ELECTROCHEMILUMINESCENCE DETECTION METHOD, AND KIT FOR ELECTROCHEMILUMINESCENCE DETECTION

REFERENCE TO A SEQUENCE LISTING

In accordance with 37 CFR § 1.831-1.835 and 37 CFR § 1.77(b)(5), the specification makes reference to a Sequence Listing submitted electronically as a .xml file named "20240807_sequence_listing_v2_553523US". This .xml file was generated on Aug. 7, 2024, and is 7,458 bytes in size. The entire contents of the Sequence Listing are hereby incorporated by reference.

CROSS-REFERENCE TO RELATED APPLICATIONS

This application is based upon and claims the benefit of priority from Chinese Patent Application No. 202310685007.0, filed on Jun. 9, 2023, the entire contents of all of which are incorporated herein by reference.

FIELD

Embodiments described herein relate generally to a method for producing an electrochemiluminescent nanoprobe, the electrochemiluminescent nanoprobe, an electrochemiluminescent sensor, an electrochemiluminescence detection method, and a kit for electrochemiluminescence detection.

BACKGROUND

Electrochemiluminescence (ECL) is an electrochemical energy relaxation process in which the excitation mode and signal detection are separated, and thus has characteristics of electrochemical controllability and low background. Because of the relatively simple temporal and spatial control of electrochemiluminescence technology, electrochemiluminescence imaging, which utilizes a charge-coupled device (CCD) camera to collect signals, has rapidly developed and is used to analyze various target molecules and is widely applied in research of genotoxin screening, immunoassay, fingerprint analysis, cell detection, and reaction mechanisms. An electrochemiluminescence detection method provides advantages of a chemiluminescent method, such as high sensitivity, wide linear range, convenience of observation, and simplicity of equipment, while the chemiluminescence method has incomparable advantages, such as high reproducibility, stable reagents, simple control, and a capability of allowing some reagents to be repeatedly used.

Conventional electrochemiluminescence imaging often employs inorganic complex luminescence systems such as ruthenium and iridium complexes, but the insolubility of these complexes in aqueous solutions and the cytotoxicity problems caused by heavy metals contained therein limit their application to biological analysis.

Semiconducting polymer dots (Pdots) are novel organic fluorescent materials that are widely used in biodetection, cell biology, and clinical medicine, for example, because they have characteristics such as non-toxicity, large photoabsorption cross section, high fluorescence quantum efficiency, photostability, and biocompatibility.

In conventional technologies, various attempts have been made to use semiconducting polymer dots as fluorescent probes for electrochemiluminescence detection (see Ningning Wang, Yagiang Feng, et al., "Electrochemiluminescent Imaging for Multi-immunoassay Sensitized by Dual DNA Amplification of Polymer Dot Signal", Anal. Chem., 2018, No. 90, 7708-7714, and see Guangming Li et al. "Ratiometric fluorescent detection of miRNA-21 via pH-regulated adsorption of DNA on polymer dots and exonuclease III-assisted amplification", Analytica Chimica Acta, 1232 (2022) 340450). Electrochemiluminescent sensors produced in the form of semiconducting polymer dots have advantages such as higher luminous intensity, better photostability, and better biocompatibility than conventional electrochemiluminescent platforms.

However, electrochemiluminescent platforms are used as signal detection platforms, which themselves do not have an identification function for target molecules to be measured, and generally require special probes to be blended to achieve identification and analysis for specific target molecules. Thus, the specificity/accuracy in identifying an object to be measured depends on a special probe to be blended therein. The selection of such probes and nucleic acid sequence that can be targeted are generally limited by specific requirements, that is, the accuracy/specificity of detection is limited, making it difficult to detect any nucleic acid sequence. For example, in the "Ratiometric fluorescent detection of miRNA-21 via pH-regulated adsorption of DNA on polymer dots and exonuclease III-assisted amplification", Pdots were coupled to DNA or RNA oligonucleotide probes to identify and analyze trace amounts of nucleic acid molecules.

Cas enzymes are nucleic acid recognition and cleavage enzyme proteins having a checkpoint mechanism, and thus have single base resolution accuracy. The greatest advantage of Cas enzyme-based nucleic acid detection is that utilizing the unique checkpoint mechanism of the Cas enzymes enables detection of nucleic acid to achieve single base resolution sensitivity. Furthermore, by designing and synthesizing guide RNA (gRNA) for the Cas enzymes, any nucleic acid sequence can be detected at low cost.

For example, a Cas12a-based electrochemiluminescence biosensor was designed and used to detect human papillomavirus (HPV-16) DNA in a prior art (see Peng-Fei Liu et al., "Cas12a-based electrochemiluminescence biosensor for target amplification-free DNA detection", Biosensors and Bioelectronics, 176, (2021), 112954).

This technique has ultrahigh accuracy in nucleic acid identification, but the sensitivity to identify trace amounts of nucleic acids is insufficient. Thus, it is generally necessary to pre-amplify nucleic acids to improve detection limits. The use of pre-amplification increases the sensitivity of detection, but decreases the accuracy of detection. This is because the amplification of a large number of nucleic acid fragments may cause aerosol contamination, which causes false positive results. The pre-amplification step also complicates the detection step and extends the detection time.

DETAILED DESCRIPTION

Figure 1:
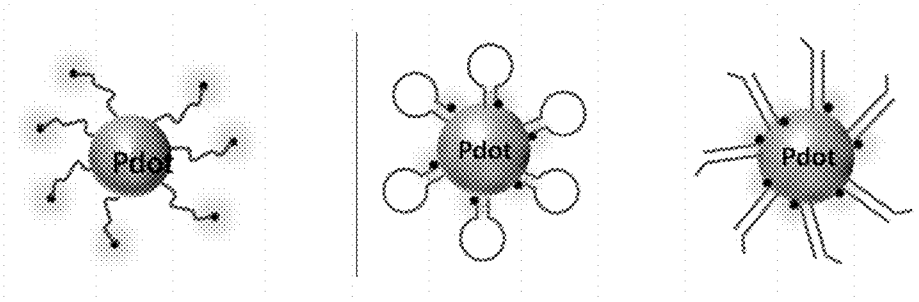
FIG. 1 is a schematic diagram illustrating structure examples of nanoprobes according to an embodiment.

The problem to be solved by embodiments described herein is to provide a method for producing an electrochemiluminescent nanoprobe having high sensitivity, high accuracy and specificity, and high flexibility without the need for amplification, the electrochemiluminescent nanoprobe, an electrochemiluminescent sensor, an electrochemiluminescence detection method, and a kit for electrochemiluminescence detection.

A method for producing an electrochemiluminescent nanoprobe according to an embodiment includes: a Pdots nanoparticle synthesis step of synthesizing a Pdots nanoparticle by polymerizing a conjugated polymer and a copolymer molecule; and a Pdots nanoparticle modification step of modifying a resulting Pdots nanoparticle using an oligonucleotide chain modified with a quencher molecule.

As described above, the Cas enzyme has the advantage of being able to target any nucleic acid fragment, but the sensitivity thereof is limited, and thus the sensitivity needs to be increased in combination with other techniques (e.g., commonly used pre-amplification). However, as described above, this may cause false positives, which also makes it difficult to quantify the original nucleic acid. An electrochemiluminescence method such as an electrochemiluminescence detection method based on semiconducting polymer dots (Pdots) has advantages of capability of signal amplification, high accuracy, and capability of quantification, and can avoid false positives due to aerosols without the need for pre-amplification. However, these advantages highly depend on the oligonucleotide probe blended and used, the accuracy/specificity of detection is limited, and it is difficult to detect any nucleic acid sequences.

The present invention was made in view of the above situation, and it is an object of the present invention to provide an electrochemiluminescence detection method having high sensitivity, high precision and specificity, and high flexibility.

As a result of conducting intensive research on the problems existing in the above conventional technologies, the inventors of the present invention found that, by applying a Cas enzyme system to the electrochemiluminescence method based on semiconducting polymer dots (Pdots), an electrochemiluminescence detection method based on the Cas enzyme can be constructed, and deficiencies in both of the Pdots-based ECL and the Cas 12-based method can be complemented, whereby an electrochemiluminescence detection method having high sensitivity, high accuracy and specificity, and also having high flexibility without the need for amplification can be provided.

Specifically, a target nucleic acid is identified by a complex of Cas protein and crRNA (Cas protein-crRNA) to activate Cas enzyme activity, and an oligonucleotide chain (Q-DNA) modified with a quencher molecule is used to modify a Pdots particle and prepare a nanoprobe, and the Q-DNA on the nanoprobe is cleaved by using the cleavage activity of the Cas protein-crRNA activated by the target, whereby the Pdots ECL signal switch can be controlled. Using the dual enzyme catalytic system with the Cas enzyme and exonuclease III (hereinafter also referred to as "EXO III") further increases the sensitivity of the Pdots ECL signal switch even more.

The present invention can provide an electrochemiluminescence detection method having high sensitivity, high accuracy and specificity, and also having high flexibility without the need for amplification. Specifically, (1) Combining a Pdots nanoprobe with collateral cleavage activity of the Cas enzyme can improve detection sensitivity for the target nucleic acid without the need for pre-amplification;

(2) The single base resolution specificity of the Cas enzyme improves the accuracy of ECL signal detection, and can avoid a false positive signal due to misidentification of the target nucleic acid;

(3) Customized Cas enzyme guide RNA (crRNA) allows targeting any nucleic acid sequence and outputting a highly sensitive signal based on ECL;

(4) When a quench group is to be coupled by a dsDNA rigid structure, it is desirable to employ a dual enzyme catalytic system of Cas12 and EXO III to broaden the range of application of Cas12 enzyme cleavage and to further improve the sensitivity of ECL detection; and (5) The ECL nanoprobe herein can be fabricated into a disposable detection chip, which is useful for point-of-care testing (POCT) and convenient, and allows rapid nucleic acid detection.

Specific embodiments of the present invention will now be described in detail. The description of the following embodiments is intended only to explain the inventive concept of the present invention and is not intended to limit the present invention.

Electrochemiluminescent Nanoprobe and Production Method Thereof

One embodiment described herein relates to a method for producing an electrochemiluminescent nanoprobe (hereinafter also referred to as "ECL nanoprobe"), the method including: a Pdots nanoparticle synthesis step of synthesizing a Pdots nanoparticle by polymerizing a conjugated polymer and a copolymer molecule; and a Pdots nanoparticle modification step of modifying a resulting Pdots nanoparticle using an oligonucleotide chain modified with a quencher molecule.

Semiconducting Polymer Dots

Semiconducting polymer dots (hereinafter also referred to as "Pdots") are nanoparticles having a small particle size (typically 20 to 30 nm in diameter), mainly formed of n-conjugated polymers, and having high brightness.

The conjugated polymers are classified according to the main chain structures into polyacetylene, polythiophene, polyaniline, polypyrrole, polyparaphenylene, polyfluorene, polyphenylenevinylene, and the like. The main chain structures of the conjugated polymers commonly used currently are illustrated in the structural formula of chemical formula (1) below.

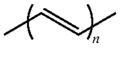
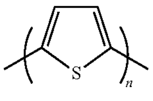
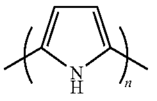
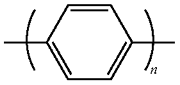
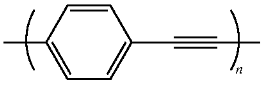
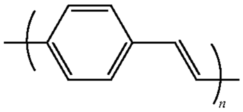
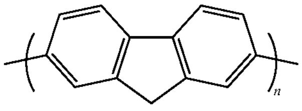
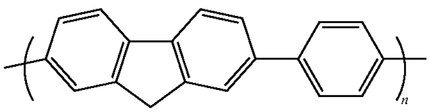
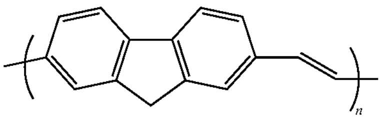

Specific conjugated polymers are not limited to particular one, and conjugated polymers described in Angew. Chem. Int. Ed. 2013, 52, 3086-3109 may be used, which may be compounds selected from PDHF, PFO, PPE, MEH-PPV, PFPV, PFBT, CN-PPV, PF-DBT5, and PBOC illustrated in chemical formula (2) below, for example.

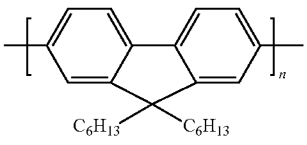

PDHF

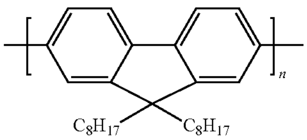

PFO

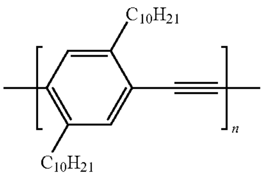

PPE

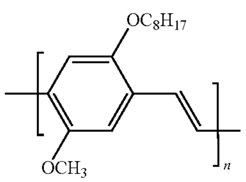

MEH-PPV

-continued

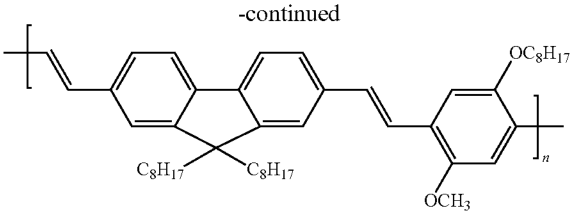

PFPV

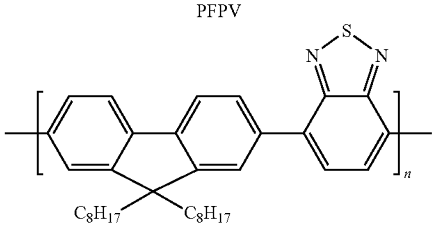

PFBT

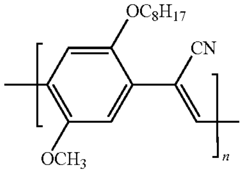

CN-PPV

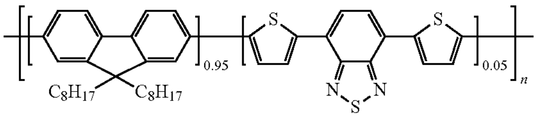

PF-DBT5

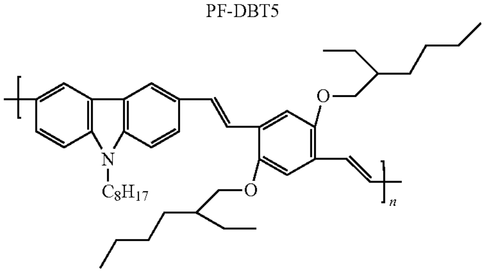

PBOC

The conjugated polymers listed above are merely examples, and as will be apparent to the skilled person, derivatives formed by replacing the above compounds with one or more substituents (e.g., alkyl groups, hydroxy groups, halogens), and their spatial isomers or the like can be used in the present embodiment as well.

The method of producing the conjugated polymers used in the present embodiment is not limited to a particular one, the synthesis can be performed by chemical reaction through synthetic routes such as Suzuki coupling reaction, Scherrer coupling reaction, and cross-coupling reaction, or the conjugated polymers can be purchased through commercial channels, which are not limited to a particular one.

Synthesis of Pdots Nanoparticle

In the present embodiment, the Pdots nanoparticle is synthesized by polymerizing a conjugated polymer and a copolymer molecule.

Nanoparticles in the present embodiment refer to particles that are nano-sized (0.1 to 100 nm) in at least one dimension in three-dimensional space. The nanoparticles may specifically be in various geometric forms such as nanoballs, nanotubes, nanorods, or nano-onions. Forming semiconducting polymer dots in a nano-form can effectively amplify the ECL response signal and improve the detection limit, detection range, selectivity, and stability of the ECL sensor. In the present embodiment, as described in Examples below, materials in a nanoball form were successfully produced. However, nanoparticles that can be used in the present embodiment are not limited to nanoballs, and can be formed in other nano-forms such as nanorods, depending on the compound raw materials and synthetic route employed.

In the present embodiment, the conjugated polymer and the copolymer molecule can be synthesized by a known method of producing an organic material nanostructure in the conventional technologies such as, but not limited to, nanocoprecipitation, microemulsion, and self-assembly methods (Ronghua Liu, "Production and Application of Novel Fluorescent Conjugated Polymer Nanoparticles", University of Science and Technology Beijing, Doctoral Dissertation, 2018). Herein, from the viewpoint of biocompatibility, the microemulsion and nanocoprecipitation methods are more preferably used.

In the microemulsion method, luminescent molecules are coated with non-toxic nonimmunogenic hydrophilic polymers, examples of which include: polyethylene glycol (PEG); polyethylene glycol-based molecules such as polyethylene glycol-phosphatidylethanolamine (PEG-PE); and biopolymers such as phospholipids, whereby highly biocompatible and highly stable luminescent molecular nanoparticles can be obtained.

In the nanocoprecipitation method, luminescent molecules (conjugated polymers) are dissolved in a good solvent, a large amount of poor solvent is injected under ultrasonic conditions, the solubility of the luminescent molecules decreases rapidly and they aggregate, thereby precipitating in the form of small particles. Subsequently, by removing the residual organic solvent, luminescent molecular nanoparticles are obtained. The nanocoprecipitation method is preferred because it is easier to operate and the nanoparticles produced are smaller and more uniform in size.

In the nanocoprecipitation method, an amphiphilic polymer can be used to surface functionalize the luminescent molecular nanoparticles. In the production process, the luminescent molecules and the amphiphilic polymer self-assemble, and one end of the amphiphilic polymer has a hydrophobic functional group and the other end thereof has a hydrophilic functional group. Thus, luminescent molecular nanoparticles coated with the amphiphilic polymer can be obtained, and the functional groups of the amphiphilic polymer (e.g., amino and carboxy groups) are exposed on the outer surface of the nanoparticles, whereby surface-functionalized luminescent nanoparticles can be obtained. Functional groups such as nucleic acids, polypeptides, sugars, or proteins react with functional groups exposed on the outer surfaces of the nanoparticles of the above amphiphilic polymer by condensation reaction or bioorthogonal click reaction, whereby luminescent molecular nanoparticles having an identification function can be obtained.

In the present embodiment, the above amphiphilic polymer is also referred to as copolymer molecule. As the copolymer molecule, commonly used copolymer molecules in this field, such as polystyrene-polyacrylic acid block copolymer (PS-PAA), polystyrene-maleic anhydride copolymer (PSMA), or poly(isobutylene-alt-maleic anhydride) (PIMA) illustrated in chemical formula (3) below, for example can be used, which are not limited to a particular one.

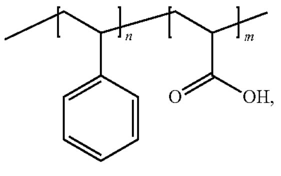

PS-PAA

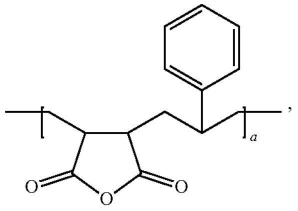

PSMA

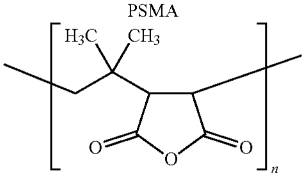

PIMA

The diameter of nanoparticles obtained by the nanocoprecipitation method can reach 1 nm to 2 nm at minimum.

The surface functionalization-modification of the Pdots nanoparticle is not limited to the above modification method with the amphiphilic polymer, and other modification methods such as direct functionalization (i.e., functional groups such as alkoxy chains, amino/carboxy groups, or biomolecules having a target function are directly modified to luminescent molecules by a covalent binding method), physical coating (i.e., coating the nanoparticle with phospholipids or silicon dioxide, etc.) can be employed.

Surface functionalization of luminescent molecule nanoparticles allows each nanoparticle to have a large number of functional groups on its surface, and also can bind a large number of oligonucleotides and other biomolecules thereon, and thus the electrochemiluminescent signal can be amplified and the detection sensitivity thereof can be improved.

Modification of Pdots Nanoparticle

In the present embodiment, modification of the Pdots nanoparticle refers to oligonucleotide modification of the Pdots nanoparticle. Specifically, the above-described surface functionalized Pdots nanoparticle is modified using an oligonucleotide chain modified with a quencher molecule to obtain an oligonucleotide-modified Pdots nanoparticle (hereinafter also referred to as "ECL nanoprobe").

The method of binding the oligonucleotide to the Pdots nanoparticle is not limited to covalent binding reaction (e.g., cross-linking by $NH_2$—COOH), and may also be other binding methods such as electrostatic action and affinity adsorption.

The oligonucleotide chain used for modification may be a double-stranded oligonucleotide chain (e.g., dsDNA) or a single-stranded oligonucleotide chain (e.g., RNA, ssDNA), and can be specifically selected appropriately according to the type of Cas enzyme used.

From the viewpoint of bringing the quencher molecule into close proximity to the Pdots and enhancing amplification of the ECL signal, the oligonucleotide chain is preferably a double-stranded oligonucleotide chain, or a single-stranded oligonucleotide chain having a secondary structure capable of bringing the quencher molecule into close proximity to the Pdots, such as a single-stranded oligonucleotide chain having a hairpin structure.

The collateral cleavage activity by the Cas enzyme is nonspecific, and thus the nucleotide sequence forming the oligonucleotide chain is not limited to a particular one and may be any sequence. The length of the oligonucleotide chain is also not limited to a particular length, and it only needs to be able to bind the quencher molecule to the Pdots and generate resonance energy transfer between the quencher molecule and the Pdots particle. The design can be made with reference to various oligonucleotide chains for coupling commonly used in the conventional technologies.

When the oligonucleotide chain is a linear single-stranded oligonucleotide chain, the number of nucleotides thereof should not be excessive from the viewpoint sensitivity to cleavage by the Cas enzyme, and is preferably 3 to 20, more preferably 4 to 11, even more preferably 5, 6, 7, 8, 9, 10, 11 or 12.

When the oligonucleotide chain is a single-stranded oligonucleotide chain having a hairpin structure, the number of nucleotides thereof may be, for example, 20 or more, and the number of nucleotides in a ring-shaped fragment forming the hairpin is not limited to a particular one as long as a ring shape is formed. From the viewpoint of sensitivity to cleavage by the Cas enzyme, the number of nucleotides in a stem fragment forming the hairpin should not be excessive, and is preferably 4 to 20, more preferably 4 to 10, and even more preferably 4, 5, 6, 7, or 8.

When the oligonucleotide chain is a double-stranded oligonucleotide chain, the double-stranded oligonucleotide chain preferably includes a chain that is directly bound to the Pdots and a chain that is indirectly bound to the Pdots by hybridization. The chain directly bound to the Pdots preferably includes a single-stranded terminal portion that can be cleaved by the Cas enzyme, a hybrid chain, a double-stranded portion that can be cleaved by a DNA exonuclease forming the double-stranded portion. From the viewpoint of sensitivity to cleavage by the Cas enzyme and the DNA exonuclease, the number of nucleotides in the single-stranded terminal portion in the double-stranded oligonucleotide chain is preferably 3 to 20, more preferably 4 to 10, even more preferably 4, 5 or 6. The number of nucleotides in the double-stranded portion in the double-stranded oligonucleotide chain, as a single chain, is preferably 15 to 24, more preferably 16 to 20, even more preferably 17, 18 or 19.

The oligonucleotide chain of the present embodiment is modified with a quencher molecule. Dynamic quenching of the quencher molecule occurs by fluorescence resonance energy transfer (FRET) or collisional quenching. Because the optical absorption of the quencher molecule overlaps the fluorescent emission of the Pdots nanoparticle, resonance energy can be transferred from the excited nanoparticle to the quencher molecule, which can quench the emission of the conjugated polymer molecule.

As the quencher molecule, any quencher molecule having resonance energy transfer properties commonly used in this field can be used and, but not limited to, for example, black hole quenchers (Black Hole Quencher™ reagents, i.e., BHQ series quenchers), dark quenchers (e.g. DABCYL series quenchers), BlackBerry™ quenchers (i.e. BBQ series quenchers), Blueberry quenchers (i.e. BLU series quenchers), or amine reactive quenchers (QSY series quenchers) can be used. Among these, the BHQ quenchers are often used. All of these quenchers are commercially available (e.g., LGC, BiochTechnologies™).

The method of binding the quencher molecule to the oligonucleotide is not limited to a particular one, and methods commonly in this field can be used. The quencher molecule may be bound to the end of the oligonucleotide or inserted into the oligonucleotide sequence.

In the present embodiment, the oligonucleotide modified with the quencher molecule functions as the signal switch of the present embodiment together with the Cas enzyme described below. Specifically, if the oligonucleotide has not been cleaved by the activated Cas enzyme, the quencher molecule is coupled to the surface of the Pdots nanoparticle with the oligonucleotide interposed therebetween and exerts a quenching effect on the Pdots, causing the sensor electrode to display low ECL intensity (ECL OFF). If the oligonucleotide has been cleaved by the activated Cas enzyme, the quencher molecule is separated from the surface of the Pdots nanoparticle, thereby causing the sensor electrode to display a strong ECL signal (ECL ON).

Electrochemiluminescent Sensor

The electrochemiluminescent sensor (hereafter, also referred to as ECL sensor) of the present embodiment can be obtained by dropping the above ECL nanoprobe onto a working electrode.

As the working electrode used in the present embodiment, but not limited to, one of electrodes commonly used for ECL detection, such as a glass carbon electrode (GCE), an indium tin oxide (ITO) electrode, or a screen-printed electrode (SPE) can be used. The indium tin oxide electrode is preferably used, and a three-electrode system is more preferably used. In this electrode system, for example, a platinum wire counter electrode, an Ag/AgCl reference electrode, and an indium tin oxide (ITO) working electrode are disposed.

Electrochemiluminescence Detection Method

One embodiment described herein relates to an electrochemiluminescence detection method (hereinafter also referred to as "ECL detection method") based on the Cas enzyme, the method including: an enzyme reaction step of adding a sample to be measured to a Cas enzyme catalytic system containing a guide nucleic acid capable of being bound to a target nucleic acid; a Pdots chip fabrication step of fixing the above-described electrochemiluminescent nanoprobe to a working electrode; and a sample detection step of adding a reaction solution obtained at the enzyme reaction step to the working electrode and collecting and analyzing an electrochemiluminescent signal.

The ECL detection method of the present embodiment may also directly use the above-described ECL sensor (also called ECL chip) without including the above-described Pdots chip fabrication step.

The ECL detection method of the present embodiment allows detection of a target molecule in the sample to be measured. The sample to be measured may be, but not limited to, urine, blood, serum, cerebrospinal fluid, or saliva, for example. The above-described target molecule may be, but not limited to, nucleic acid, protein, or a chemical small molecule, for example.

In the present embodiment, when the target molecule is dropped as a target identification and signal conversion unit in enzyme-catalyzed reaction or other specific chemical reaction, this enzyme reaction or chemical reaction can change the signal switch state of the ECL nanoprobe, thereby achieving qualitative or quantitative detection for the target signal.

As the enzyme used in the enzyme-catalyzed reaction, a Cas enzyme having collateral cleavage activity, for example, in a CRISPR/Cas enzyme can be used. This activity belongs to nonspecific nuclease cleavage activity and, when targeted to a target nucleic acid molecule, the Cas enzyme is activated and acquires the nonspecific activity to cleave any nucleic acid molecule.

The Cas enzyme may contain at least one Cas protein selected from Cas12 (type VA), Cas13 (type VI), and Cas14 (type VF), for example, and may be at least one Cas protein selected from Cas12a, Cas12b, Cas13a, Cas13b, Cas14a, Cas14b, and Cas14c, for example. Herein, the Cas12 targets double-stranded DNA (dsDNA), the Cas13 targets single-stranded RNA (ssRNA), and the Cas14 targets ssDNA. The Cas12a also has nonspecific cleavage activity (also called trans-cleavage activity) for single-stranded DNA (ssDNA), and thus can further target ssDNA.

The Cas12 enzyme is preferred because it targets DNA, is commercially mature, and can be used in other non-nucleic acid detection areas (e.g., proteins, small biological molecules) in addition to DNA.

In the present embodiment, any nucleic acid sequence can be targeted by designing and synthesizing guide RNA (gRNA) for the Cas enzyme. The gRNA is formed of two parts, one is CRISPR RNA (crRNA) that is a nucleotide sequence having a length of 17 to 20 bases and configured to complementarily pair up with a target nucleic acid; and the other is tracr RNA that serves as a scaffold to assist folding of the Cas enzyme. The guide RNA activates the Cas enzyme by binding to The activated oligonucleotides of the target nucleic acid. Cas enzyme cleaves oligonucleotides coupled to the ECL nanoprobe by collateral cleavage activity, thereby changing the signal switch state of the ECL nanoprobe.

The principle of the signal switch and the ECL detection method of the present embodiment will be specifically described below. The principle of the signal switch of the present embodiment is as follows.

Pdots particles modified with oligonucleotide chains are used as the ECL nanoprobe in the present embodiment, and the Pdots are in the ECL OFF state because the quencher molecules are modified at the ends of the oligonucleotide chains (e.g. SSDNA, hDNA and dsDNA used in Examples). If a target molecule is not present and the Cas enzyme is not activated by the target molecule, the oligonucleotide chains modified with the quencher molecules are not separated from the Pdots surface and the sensor electrode displays low ECL intensity (ECL OFF). In contrast, if a target molecule is present and the Cas enzyme is activated, the oligonucleotide chains coupled to the Pdots are cleaved because the Cas enzyme such as Cas12 enzyme has collateral cleavage activity. This causes the quencher molecule to be separated from the Pdots surface to restore the ECL of the Pdots, and the sensor electrode generates a strong ECL signal (ECL ON).

FIG. 1 is a schematic diagram illustrating structure examples of nanoprobes according to the embodiment. FIG. 1 illustrates schematic diagrams of the respective structures of a Pdots nanoprobe modified with linear single-stranded DNAS (ssDNA-Pdots), a Pdots nanoprobe modified with single-stranded DNAs in a hairpin structure (hDNA-Pdots), and a Pdots nanoprobe modified with double-stranded DNAs (dsDNA-Pdots).

As illustrated in FIG. 1, a quencher molecule is coupled to an end of each oligonucleotide (DNA) chain, and in the structures of hDNA-Pdots and dsDNA-Pdots, the quencher molecules are closer to the Pdots, which provides better signal quenching effect and stronger signal amplification, and thus better detection sensitivity is expected.

Figure 2:
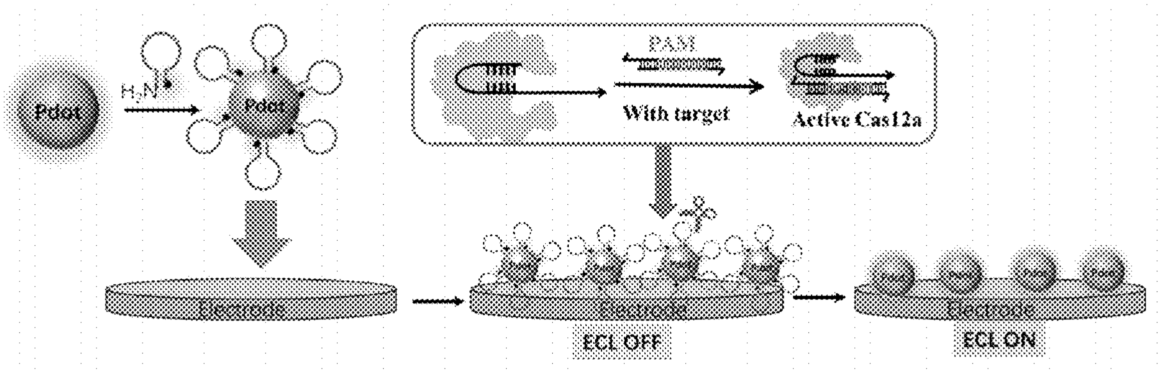
FIG. 2 is a schematic diagram of target nucleic acid detection illustrating an ECL switch principle based on a hDNA-Pdots nanoprobe.

When the hDNA-Pdots is used as a reporter probe, only a Cas enzyme needs to be used for the enzyme reaction. As illustrated in FIG. 2, hDNA itself is a single-stranded DNA fragment, and when a target molecule is present and the Cas enzyme is activated, the hairpin ring-shaped single-stranded fragment is first cleaved by the collateral cleavage activity of the Cas enzyme. After the single-stranded fragment of the hairpin is cleaved, the double-stranded portion bound by hydrogen bonds becomes weak in bonding strength and the hybridization is eliminated, whereby the BHQ is separated from the Pdots surface, the ECL of the Pdots is restored, and the sensor electrode generates a strong ECL signal (ECL ON). FIG. 2 is a schematic diagram of target nucleic acid detection illustrating an ECL switch principle based on a hDNA-Pdots nanoprobe.

Figure 3:
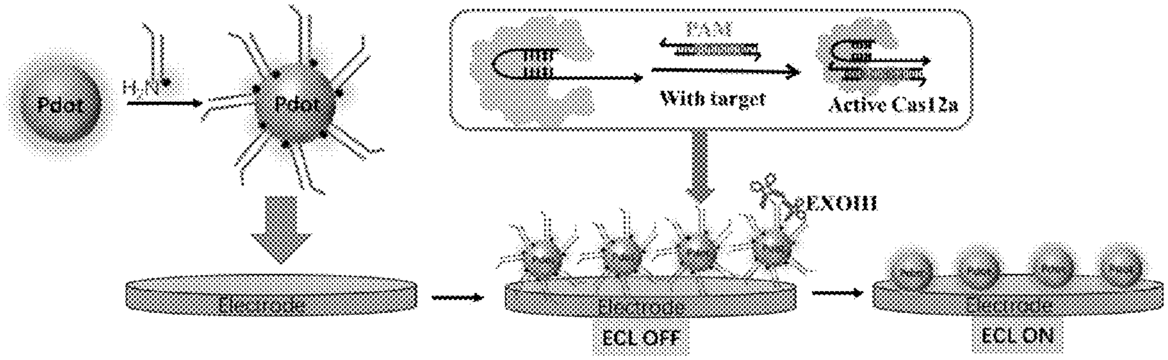
FIG. 3 is a schematic diagram of target nucleic acid detection illustrating a dual enzyme-catalyzed ECL switch principle based on a dsDNA-Pdots nanoprobe.

When the dsDNA-Pdots nanoprobe is used as a reporter probe, it is necessary to use a dual enzyme catalytic system of the Cas enzyme and DNA exonuclease III for the enzyme reaction. As illustrated in FIG. 3, when a target molecule is present and the Cas enzyme is activated, the shorter single-stranded fragment exposed at the outer end of dsDNA is first cleaved. Furthermore, the exonuclease III is activated to cleave the remaining double-stranded fragment, whereby the quencher molecule is separated from the surface of the Pdots, the ECL of the Pdots is restored, and the sensor electrode generates a strong ECL signal (ECL ON). FIG. 3 is a schematic diagram of target nucleic acid detection illustrating a dual enzyme-catalyzed ECL switch principle based on a dsDNA-Pdots nanoprobe.

The above description of the DNA-Pdots nanoprobes is merely an example, and as known by the skilled person, oligonucleotides that can be used in the present embodiment are not limited to DNA and may be RNA or the like, and the Cas enzyme is not limited to Cas12a illustrated in FIGS. 2 and 3, and other types of Cas12 enzymes or Cas13 and Cas14 enzymes can be used as well. The enzyme for cleaving the above-described double-stranded DNA is not limited to EXO III, and other cleavage enzymes available in this field may also be used.

The specific steps of the ECL detection method of the present embodiment are, for example, as follows.

Enzyme reaction step: A sample to be measured is added to a Cas enzyme system containing Cas protein and crRNA to obtain a sample reaction solution. At this step, this crRNAs can specifically identify a target nucleic acid in the sample to be measured.

Pdots chip fabrication step: The ECL nanoprobe of the present embodiment is dropped onto a working electrode to obtain a Pdots chip (i.e., ECL sensor, Pdots ECL chip). It should be understood that the ECL sensor of the present embodiment can also be used directly without producing the ECL chip at the time of use. The ECL sensor is preferably a disposable detection chip (also referred to as "Pdots disposable detection chip" in the present embodiment). It can be obtained by fixing the ECL nanoprobe of the present embodiment to a screen-printed electrode.

Sample detection step: The sample reaction solution is dropped onto the Pdots chip, incubated at a certain temperature for a certain time, and then an electrochemiluminescent signal is collected to be analyzed. The above-described signal switch enables the ECL detection of the present embodiment.

Kit for Electrochemiluminescence Detection

One embodiment described herein relates to a kit for electrochemiluminescence detection based on the Cas enzyme (hereinafter also referred to as "ECL detection kit"), the kit including: an enzyme reaction solution containing the Cas enzyme catalytic system containing a guide nucleic acid capable of being bound to a target nucleic acid; and the Pdots disposable detection chip including the above-described electrochemiluminescent nanoprobe fixed on a screen-printed electrode.

As described above, when the oligonucleotide chain in the ECL nanoprobe of the present embodiment is double-stranded DNA, the enzyme reaction solution may further contain an EXO III enzyme.

The ECL detection kit of the present embodiment may also include other reagents and instruction manuals necessary for ECL detection.

The electrochemiluminescent nanoprobe, the production method thereof, applications thereof, and the like have been described above based on the embodiments, but the present invention is not limited to these. As long as not departing from the gist of the present invention, forms obtained by various modifications of the embodiments that the skilled person can conceive and other forms constructed by combining some components in the embodiments are also included in the scope of the present invention.

EXAMPLES

Examples will be provided below to specifically describe the Pdots nanoparticle, the ECL nanoprobe, the ECL detection method, and the like of the embodiments. Note that the present invention is not limited to these Examples.

The reagents used in Examples, the test methods and apparatus used therein are as follows (1) Reagents EnGen (registered trademark) Lba Cas12a was purchased from New England Biolabs (Ipswich, MA, UK).

Polystyrene maleic anhydride (PSMA, average Mw: 1700), 4-(2-hydroxyethyl)-1-piperazine ethanesulfonic acid (HEPES), polyethylene glycol (PEG, average Mw: 3350), and 1-(3-(dimethylamino) propyl)-3-ethylcarbodiimide hydrochloride (EDC) were all purchased from Sigma-Aldrich Co., Ltd. (Shanghai, China).

Poly[(9,9-dioctylfluorenyl-2,7-diyl)-co-(1,4-benzo-{2,1',3}-thiazole)] (PFBT) and tripropylamine (TPrA, 98%) were purchased from J&K Chemical Ltd. (Beijing, China).

Disposable screen-printed electrodes were purchased from Nanjing Jingjie Biotechnology Co., Ltd. (Nanjing, China).

All oligonucleotides listed in Table 1 were purchased from Sangon Bioengineering Co., Ltd. (Shanghai, China).

Phosphate buffer solution (PBS, 0.1 M, pH 7.4) was prepared by mixing $KH_2PO_4$ and $Na_2HPO_4$ storage solutions.

The oligonucleotide sequences used in the examples were as follows.

TABLE 1

| SEQUENCE No. | NAME | SEQUENCE (5'-3') |
|---|---|---|
| 1 | HPV 16-TS | AAT ATG TCA TTA TGT GCT GCC ATA TCT ACT TCA GAA ACT |
| 2 | HPV 16-NTS | AGT TTC TGA AGT AGA TAT GGC AGC ACA TAA TGA CAT ATT |
| 3 | ssDNA | $NH_2$-$C_6$-TT TTT ATT TTT-BHQ2 |
| 4 | Hairpin DNA | 5'-BHQ2-TTTTTTTTTACCATTTTTTTAACT TATTTGGTTCAGCG TTCCTTT-$NH_2$-3' |
| 5 | crRNA (HPV16) | UAA UUU CUA CUA AGU GUA GAU UGA AGU AGA UAU GGC AGC AC |
| 6 | dsDNA-1 | 5'-$NH_2$-$(CH_2)_6$-TTTTTAGCAACCTCAAACT TATT-3' |
| 7 | dsDNA-2 | 5'-GTTTGAGGTTGCTAAAAA-BHQ2-3' |

(2) Test Methods and Apparatus

Transmission electron microscope (TEM) images was obtained by TECNAIG2F 20 transmission electron microscope (FEI, USA).

Zeta potential was recorded with 90 Plus DynaPro NanoStar (Brookhaven Instrument Corporation, USA).

UV absorption spectra were obtained by UV-3600 spectrophotometer (Shimadzu, Japan).

Cyclic voltammetry tests were performed in a CHI 630D electrochemical workstation (CHI instruments Inc., China).

ECL tests were performed in a homemade reaction tank of MPI-EII ECL analyzer (Xi'an Remex, China) using a three-electrode system.

Example 1: Production of ECL Nanomaterials

1. Production of PFBT Pdots

For the production process, texts in Anal. Chem., 2018, 90, 7708-7714 published by the inventors were referred.

To begin with, 1 mg of PFBT and PSMA were each dissolved in 1 mL of tetrahydrofuran (THF) to prepare 1 mg/mL of PFBT and PSMA. Subsequently, 500 μL of PFBT (1 mg/mL) and 100 μL of PSMA (1 mg/mL) were taken and added to 9.4 mL of THE to be mixed, and the resulting solution was degassed by sonication for 20 minutes to obtain a precursor solution. 2 mL of the precursor solution was quickly injected at five more times each into 8 mL of ultrapure water under ultrasonic conditions and sonicated for 3 minutes, and then excess ultrapure water and tetrahydrofuran were removed by rotary distillation. Finally, the PFBT-Pdots were filtered with a polyethersulfone syringe having a pore diameter of 0.22 μm, whereby PFBT Pdots were produced.

Figure 4:
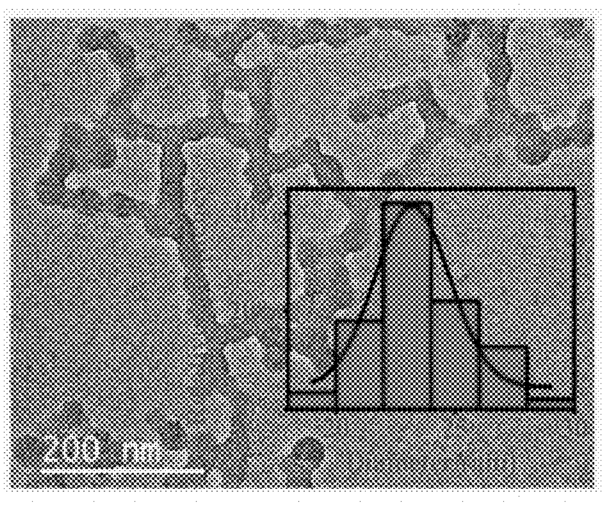
FIG. 4 is a diagram illustrating results of TEM analysis of PFBT Pdots produced in Example 1.

The morphology of the produced PFBT Pdots was analyzed by a transmission electron microscope (TEM) and the results are illustrated in FIG. 4. FIG. 4 is a diagram illustrating the results of TEM analysis of PFBT Pdots produced in Example 1. As illustrated in FIG. 4, the Pdots particles had a good regular spherical shape and were uniform in size, with an average particle size of 24±2 nm.

2. Production of ECL Nanoprobes

1) Production of PFBT Pdots Probes Modified with Nucleic Acids a. Production of ssDNA-Pdots 600 μL of PFBT Pdots, 12 μL of 5% PEG, and 12 μL of 1 M HEPES were taken and vibrated to be mixed uniformly, and then the PH was adjusted to 7.3 with 0.1 M NaOH. Furthermore, 12 μL of 10 mg/mL EDC and 3 μL of 10 mg/mL NHS were added, and the resulting solution was oscillated for 30 minutes to be mixed uniformly. Subsequently, 10 μL of 100 UM ssDNA was added, the resulting solution was stirred at 200 rmp for 48 hours, and then free ssDNA was removed by ultrafiltration in a 30 kd ultrafiltration tube (10000 rmp, 5 min/time, repeated 8 times), whereby ssDNA-Pdots were obtained.

b. Production of hDNA-Pdots

600 μL of PFBT Pdots, 12 μL of 5% PEG, and 12 μL of 1 M HEPES were taken and vibrated to be mixed uniformly, and then the PH was adjusted to 7.3 with 0.1 M NaOH. Furthermore, 12 μL of 10 mg/mL EDC and 3 μL of 10 mg/mL NHS were added, and the resulting solution was oscillated for 10 minutes to be mixed uniformly. Subsequently, 10 μL of 100 UM hairpin DNA was added, the resulting solution was stirred at 200 rmp for 48 hours, and then free hairpin DNA was removed by ultrafiltration in a 30 kd ultrafiltration tube (10000 rmp, 5 min/time, repeated 8 times), whereby hDNA-Pdots were obtained.

c. Production of dsDNA-Pdots

600 μL of PFBT Pdots, 12 μL of 5% PEG, and 12 μL of 1 M HEPES were taken and vibrated to be mixed uniformly, and then the PH was adjusted to 7.3 with 0.1 M NaOH. Furthermore, 12 μL of 10 mg/mL EDC and 3 μL of 10 mg/mL NHS were added, and the resulting solution was oscillated for 10 minutes to be mixed uniformly. Subsequently, 60 μL of 15.5 UM dsDNA was added, the resulting solution was stirred at 200 rmp for 48 hours, and then free dsDNA was removed by ultrafiltration in a 30 kd ultrafiltration tube (10000 rmp, 5 min/time, repeated 8 times), whereby dsDNA-Pdots were obtained.

To all of the above-described ssDNA, hairpin DNA, and dsDNA, the quencher molecule BHQ2 was coupled in advance as illustrated in Table 1.

d. Characteristic Analysis of DNA-Pdots

Figure 5A:
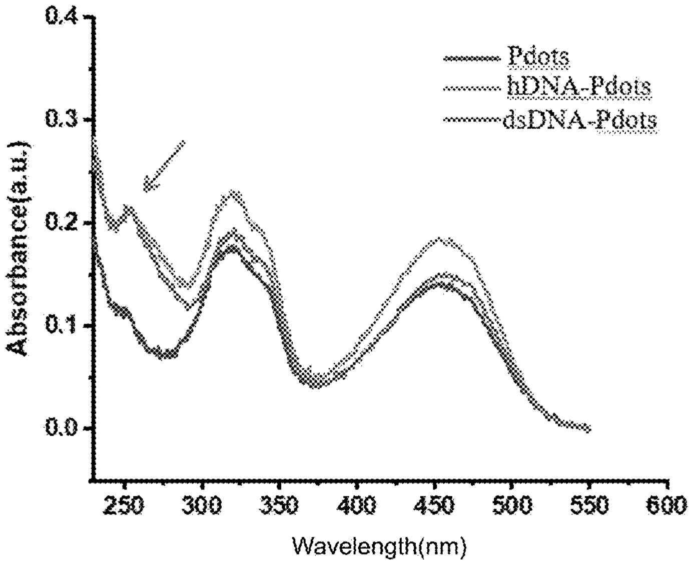
FIG. 5A is a graph illustrating results of ultraviolet analysis of DNA-Pdots produced in Example 1.
Figure 5B:
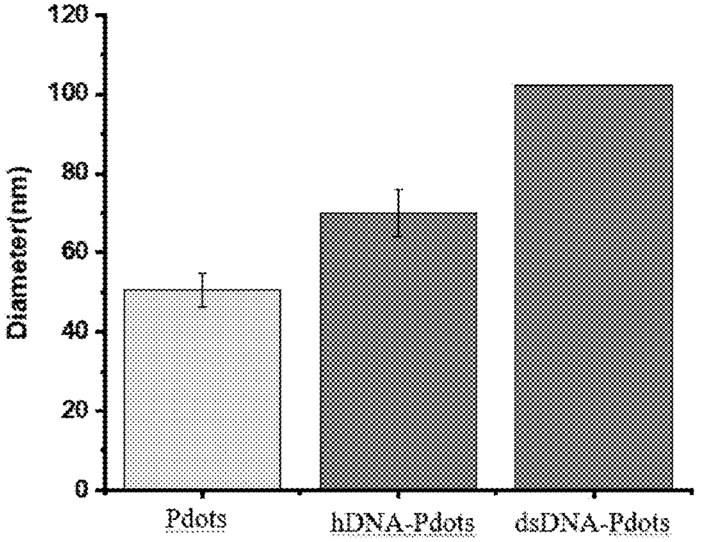
FIG. 5B is a graph illustrating results of DLS analysis of DNA-Pdots produced in Example 1.

Ultraviolet and DLS analyses were performed on the synthesized ssDNA-Pdots, dsDNA-Pdots, and hDNA-Pdots, and the results are illustrated in FIGS. 5A and 5B. FIG. 5A is a graph illustrating the results of the ultraviolet analysis of the DNA-Pdots produced in Example 1. FIG. 5B is a graph illustrating the results of the DLS analysis of the DNA-Pdots produced in Example 1.

As can be seen from FIG. 5A, ssDNA-Pdots (not illustrated), dsDNA-Pdots, and hDNA-Pdots all had a characteristic peak of DNA at 260 nm in comparison with Pdots. As can be seen from FIG. 5B, the absorption and particle size of ssDNA-Pdots (not illustrated), dsDNA-Pdots, and hDNA-Pdots all increased in comparison with Pdots. These results indicate that the syntheses of ssDNA-Pdots, dsDNA-Pdots, and hDNA-Pdots were successful.

Example 2: Verification of Signal Switch Based on Cas12a Conversion Catalyst and Detection of HPV DNA (1) Principle of Signal Switch a. Basic Principle The oligonucleotide chains (ssDNA, dsDNA, and hDNA above) are modified at their ends with BHQ, and thus Pdots are in the ECL OFF state. If a target molecule is not present and the Cas enzyme is not activated by the target molecule, the oligonucleotide chains modified with BHQ are not separated from the Pdots surface and the sensor electrode displays low ECL intensity (ECL OFF). In contrast, if a target molecule is present and the Cas enzyme is activated, the oligonucleotide chains are cleaved by collateral cleavage activity thereof. This causes the BHQ to be separated from the Pdots surface to restore the ECL of the Pdots, and the sensor electrode generates a strong ECL signal (ECL ON).

b. ECL Switch Based on ssDNA-Pdots and hDNA-Pdots Nanoprobes

In cases in which ssDNA-Pdots and hDNA-Pdots are used as reporter probes, both ssDNA and hDNA are single-stranded DNA fragments, and as described in above, when a target molecule is present and the Cas enzyme is activated, the single-stranded DNA is cleaved by collateral cleavage activity, whereby the quencher molecules are separated from the Pdots surface.

In hDNA fragments, as illustrated in FIG. 2, the ring-shaped single-stranded fragment of the hairpin is first cleaved by the Cas enzyme. After the single chain has been cleaved, the double-stranded portion bound by hydrogen bonds becomes weak in bonding strength and the hybridization is eliminated, whereby BHQ is separated from the Pdots surface, the ECL of the Pdots is restored, and the sensor electrode generates a strong ECL signal (ECL ON).

c. Dual Enzyme-Catalyzed ECL Switch Based on dsDNA-Pdots Nanoprobe

In a case in which the dsDNA-Pdots nanoprobe is used as a reporter probe, when a target molecule is present and the Cas12a enzyme is activated, a short single-stranded fragment exposed at the outer end of the dsDNA is first cleaved. Furthermore, exonuclease III (EXO III) is activated to cleave the remaining double-stranded fragment, whereby the BHQ is separated from the surface of the Pdots, the ECL of the Pdots is restored, and the sensor electrode generates a strong ECL signal (ECL ON).

(2) Verification of Signal Switches

1. Production of ECL Sensor Electrodes

2 μL of ssDNA-Pdots, hDNA-Pdots, and dsDNA-Pdots were each dropped onto a surface of a screen-printed electrode, dried, and fixed, whereby sensor electrodes of ssDNA-Pdots, hDNA-Pdots, and dsDNA-Pdots were produced.

2. Detection a. ECL Detection Based on ssDNA-Pdots or hDNA-Pdots Nanoprobe

To begin with, a sample reaction solution containing 50 nM Cas12a protein and 0.25 UM crRNA was prepared. 1 μL of HPV16 DNA was added to 19 μL of the sample reaction solution, and the resulting solution was mixed uniformly, whereby Cas12a detection solution was prepared.

Subsequently, 4 μL of Cas12a detection solution was taken and dropped onto the respective surfaces of the ssDNA-Pdots and hDNA-Pdots sensor electrodes, and the resulting products were incubated at 37 °C for 1 hour, washed with 1×PBS, and subjected to natural drying.

Finally, ECL responses were recorded in an ECL detection electrolyte (0.1 M pH 7.4 PBS containing 0.1 M TPrA and 0.1 M $KNO_3$). Here, ECL detection was performed with cyclic voltammetry by scanning from 0 to +1.50 V at a scanning speed of 100 mV/s.

b. Dual Enzyme-Catalyzed ECL Detection Based on dsDNA-Pdots Nanoprobe

To begin with, a Cas12a detection solution (10-fold diluted Buffer II containing 50 nM Cas12a, 0.25 UM crRNA, and 50 nM HPV16 DNA) was prepared as described above.

Subsequently, 4 μL of Cas12a detection solution was taken and dropped onto the surface of the dsDNA-Pdots sensor electrode, and the resulting product was incubated at 37 °C for 1 hour, washed with 1×PBS, and subjected to natural drying.

Subsequently, 3 μL of EXO III solution (10-fold diluted Buffer I containing 100 U/ml EXO III) was dropped onto the surface of the sensor electrode, and the resulting product was incubated at 37 °C for 30 minutes and washed with 1×PBS.

Finally, ECL responses were recorded in an ECL detection electrolyte (0.1 M pH 7.4 PBS containing 0.025 M TPrA and 0.1 M $KNO_3$). Specific ECL detection conditions are as follows.

Figure 6A:
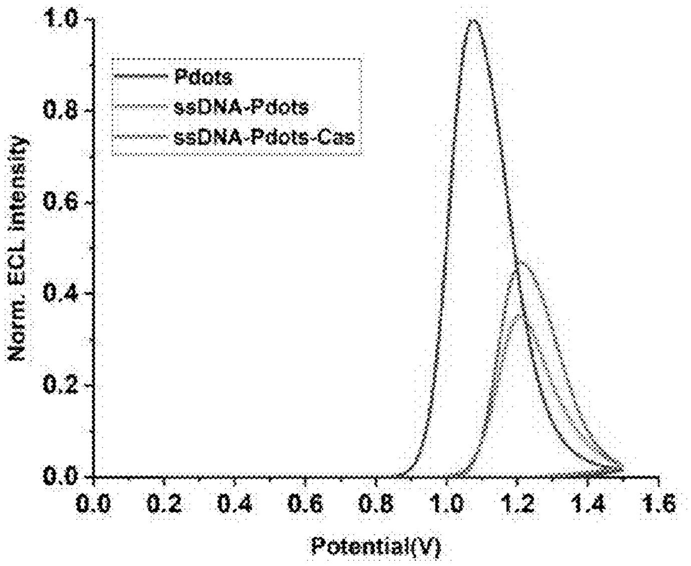
FIGS. 6A to 6C are graphs illustrating comparison results of ECL intensity before and after enzyme activation of different ECL sensor electrodes produced in Example 2.
Figure 6B:
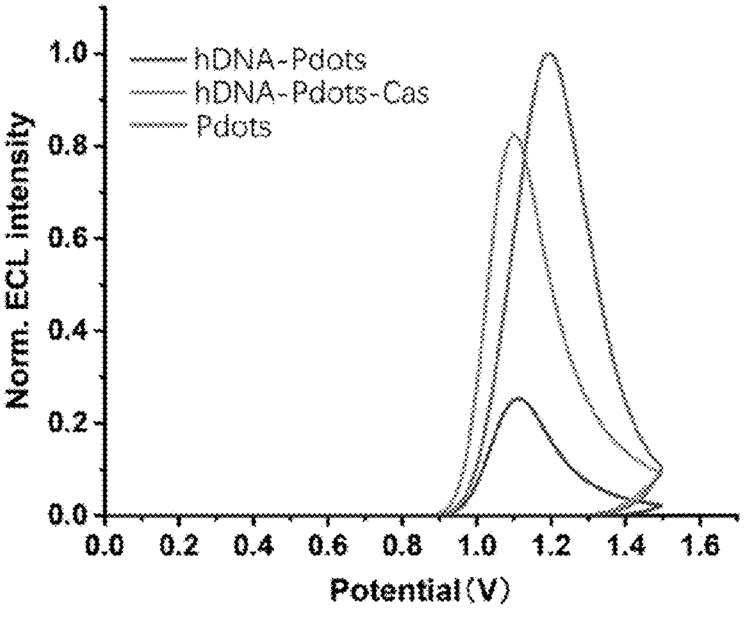
Figure 6C:
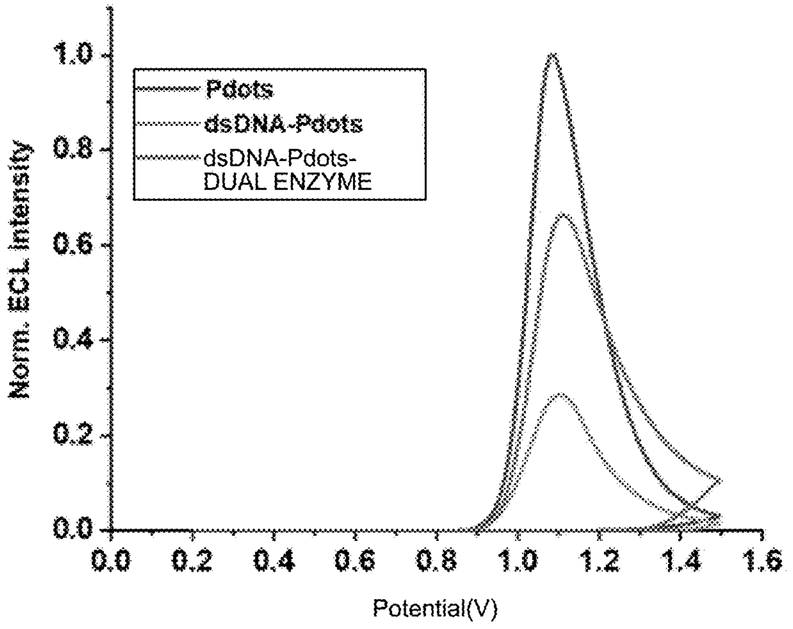

Detection method: Cyclic voltammetry method
Maximum potential: +1.5 V
Minimum potential: 0 V
Scanning speed: 100 mV/s
PMT: High voltage 500 V ECL detection results are illustrated in FIGS. 6A to 6C. FIGS. 6A to 6C are graphs illustrating comparison results of ECL intensity before and after enzyme activation of different ECL sensor electrodes produced in Example 2.

FIG. 6A is a graph illustrating the comparison result of ECL intensity before and after Cas enzyme activation of ssDNA-Pdots modified electrode, FIG. 6B is a graph illustrating the comparison result of ECL intensity before and after Cas enzyme activation of hDNA-Pdots modified electrode, and FIG. 6C is a graph illustrating the comparison result of ECL intensity before and after dual enzyme activation of dsDNA-Pdots modified electrode.

As can be seen from FIGS. 6A, 6B, and 6C, when the sensor electrodes modified with different Pdots nanoprobes described above were used, the ECL intensity decreased in all cases and the ECL intensity recovered in all cases after the enzyme was activated by the target nucleic acid. These results indicated the feasibility of the direct ECL switch system based on the Pdots nanoprobes of the present embodiment.

As can be seen from FIG. 6B, the ECL intensity of the hDNA-Pdots modified electrode decreased to 20% compared to the Pdots modified electrode, indicating that the sensor interface was in the ECL OFF state. When 1 UM of the target molecule was added, the Cas12a enzyme was activated, generating an ECL ON response and restoring the ECL intensity of the modified electrode to 80%. In other words, the hDNA-Pdots-modified electrode displayed better detection sensitivity than the ssDNA-Pdots-modified electrode. From this result, it can be considered that a better signal quenching effect and stronger signal amplification were obtained in ssDNA having a hairpin structure because the quencher molecules were closer to the Pdots.

As can be seen from FIG. 6C, the ECL intensity of the dsDNA-Pdots modified electrode decreased to 30% compared to the Pdots modified electrode, indicating that the sensor interface was in the ECL OFF state. When 1 μM of the target molecule was added, the Cas12a enzyme was activated, triggering cleavage reaction by the Cas12a-EXO III dual enzyme, generating an ECL ON response and restoring the ECL intensity of the modified electrode to 658. This result indicated not only the feasibility of the dsDNA-Pdots nanoprobe-based dual enzyme-catalyzed ECL switch system, but also its good detection sensitivity. Since the dsDNA structure is similar to the hDNA structure, the quencher molecule is closer to the Pdots than the linear ssDNA, and thus it is considered that good detection sensitivity could be obtained similarly. Furthermore, a dual enzyme cleavage system including the Cas enzyme and exonuclease was employed for this detection, which helped in the high activity of the dual enzyme cleavage system, and the time required to obtain the ECL signal became shorter (less than 30 minutes).

c. Detection Performance Tests

Figure 7:
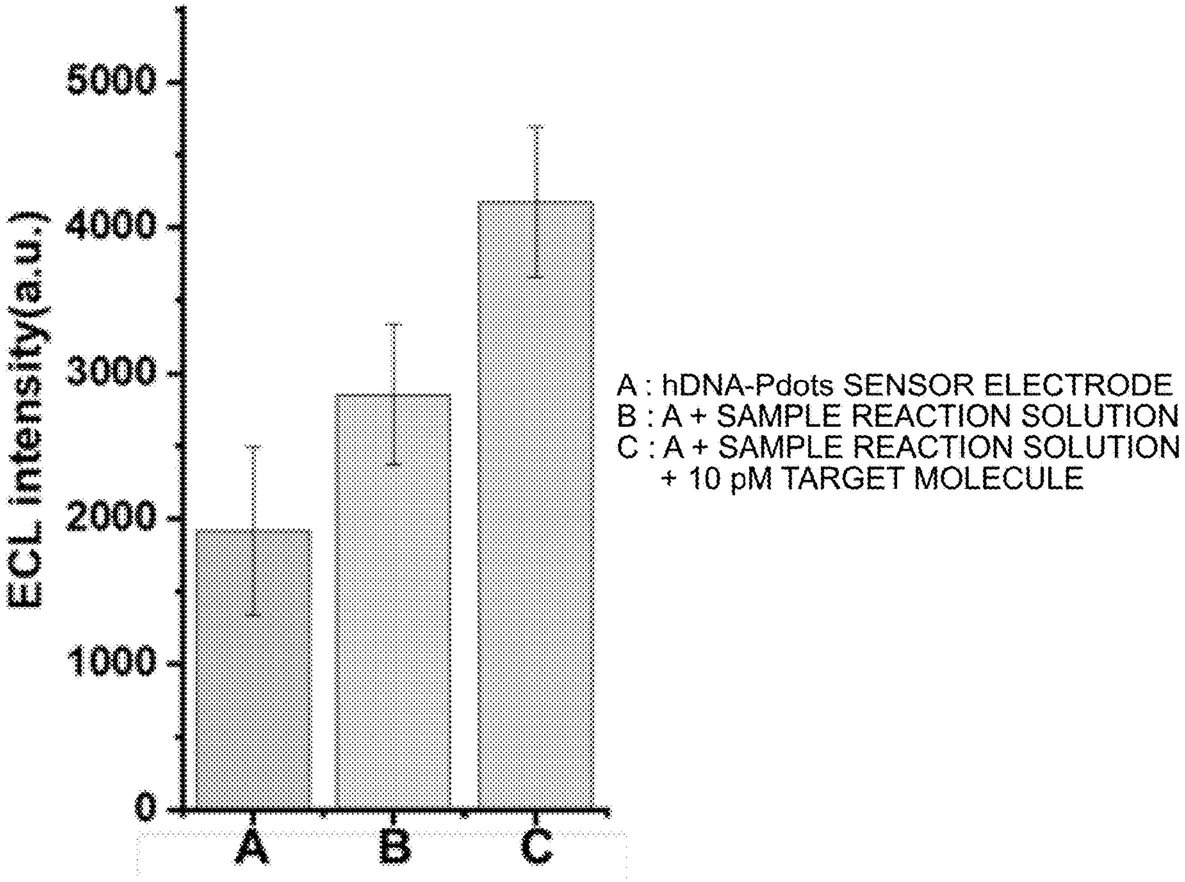
FIG. 7 is a graph illustrating results of HPV 16 DNA detection using a hDNA-Pdots sensor electrode produced in Example 2.

The hDNA-Pdots sensor electrode produced as described above was used to detect different concentrations of HPV 16 DNA. FIG. 7 is a graph illustrating results of HPV 16 DNA detection using the hDNA-Pdots sensor electrode produced in Example 2. As illustrated in FIG. 7, a response was still observed when the HPV16 DNA concentration reached 10 pM, which indicated that the produced ECL nanoprobes and ECL sensors of the embodiments described herein can be practically used to detect target nucleic acids.

INDUSTRIAL APPLICABILITY

As can be seen from the above Examples, the ECL nanoprobes, especially the hDNA-Pdots nanoprobe and the dsDNA-Pdots nanoprobe, produced in the embodiments can be combined with the Cas enzyme system to switch the ECL signal from off to on, whereby providing an electrochemiluminescence detection method having high sensitivity, high accuracy and specificity, and also having high flexibility without the need for amplification can be provided. The ECL nanoprobes can be further produced into disposable detection chips, e.g., disposable plastic chips or paper-based chips, which are useful for POCT and convenient, and allow rapid nucleic acid detection.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A production method for an electrochemiluminescence nanoprobe, the method comprising:

synthesizing a Pdots nanoparticle by polymerizing a conjugated polymer and a copolymer molecule; and modifying a resulting Pdots nanoparticle using an oligonucleotide chain modified with a quencher molecule, wherein the oligonucleotide chain comprises a single-stranded terminal portion that can be cleaved by Cas enzymes activated by a target nucleic acid and a double-stranded portion that can be cleaved by DNA exonucleases.

2. The production method of claim 1, wherein the conjugated polymer is PDHF, PFO, PPE, MEH-PPV, PFPV, PFBT, CN-PPV, PF-DBT5, or PBOC:

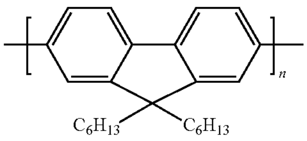

PDHF

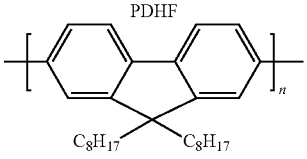

PFO

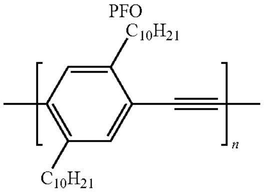

PPE

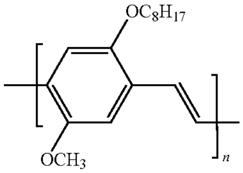

MEH-PPV

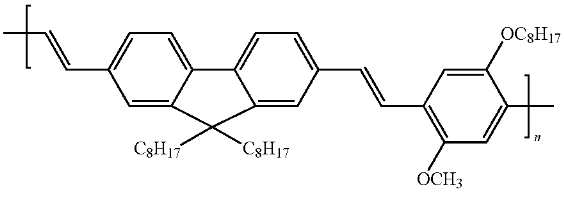

PFPV

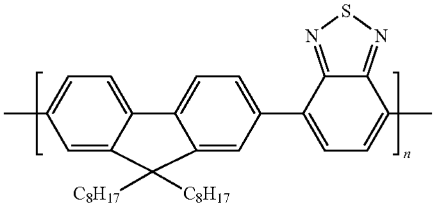

PFBT

-continued

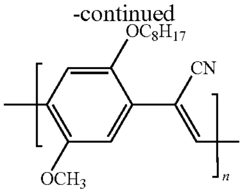

CN-PPV

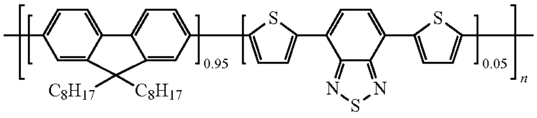

PF-DBT5

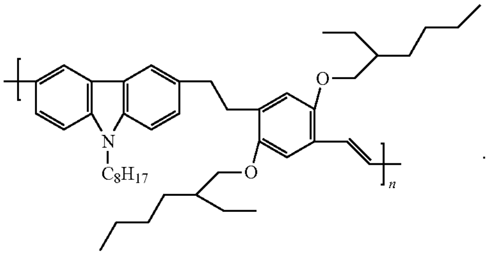

PBOC

3. The production method of claim 1, wherein the copolymer molecule is one of a polystyrene-polyacrylic acid block copolymer (PS-PAA), a polystyrene-maleic anhydride copolymer (PSMA), or poly(isobutylene-alt-maleic anhydride) (PIMA):

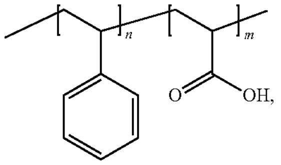

PS-PAA

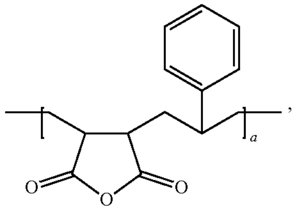

PSMA

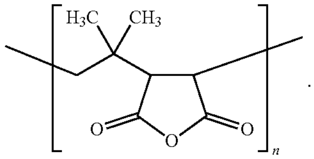

PIMA

4. The production method of claim 1, wherein the conjugated polymer and the copolymer molecule are synthesized into the Pdots particle by a nanocoprecipitation method.

5. The production method of claim 1, wherein the quencher molecule is a Black Hole Quencher, a dark quencher, or an amine reactive quencher.

6. The production method of claim 1, wherein the oligonucleotide chain comprises a hairpin structure.

7. An electrochemiluminescence nanoprobe, comprising:

a Pdots nanoparticle into which a conjugated polymer and a copolymer molecule are polymerized, wherein the Pdots nanoparticle is modified with an oligonucleotide chain modified with a quencher molecule, and wherein the oligonucleotide chain comprises a single-stranded terminal portion that can be cleaved by Cas enzymes activated by a target nucleic acid and a double-stranded portion that can be cleaved by DNA exonuclease.

8. An electrochemiluminescence sensor being a working electrode, comprising, thereon;

an electrochemiluminescence nanoprobe that is a Pdots nanoparticle into which a conjugated polymer and a copolymer molecule are polymerized has been dropped, wherein the Pdots nanoparticle is modified with an oligonucleotide chain modified with a quencher molecule, wherein the oligonucleotide chain comprises a single-stranded terminal portion that can be cleaved by Cas enzymes activated by a target nucleic acid and a double-stranded portion that can be cleaved by DNA exonuclease, and wherein the working electrode generates an electrochemiluminescent signal when the quencher molecule is separated from the Pdots surface by an effect of the Cas enzyme and an effect of the DNA exonuclease.

9. The electrochemiluminescence sensor of claim 8, wherein the working electrode is one of a glass carbon electrode, an indium tin oxide electrode, or a screen-printed electrode.

10. An electrochemiluminescence detection method comprising:

performing enzymatic reaction by adding a sample to be measured to a Cas enzyme catalytic system containing a guide nucleic acid capable of being bound to a target nucleic acid, the Cas enzyme is activated by the presence of the target nucleic acid in the sample; and performing sample detection, comprising:

adding a reaction solution obtained at the performing enzymatic reaction to a working electrode on which an electrochemiluminescence nanoprobe that is a Pdots nanoparticle, into which a conjugated polymer and a copolymer molecule are polymerized, the Pdots nanoparticle being modified with an oligonucleotide chain modified with a quencher molecule, the oligonucleotide chain comprising a single-stranded terminal portion that can be cleaved by Cas enzymes activated by a target nucleic acid, has been dropped, thereby the activated Cas enzyme cleaves the oligonucleotide chain; and collecting and analyzing an electrochemiluminescent signal generated by separating the quencher molecule from the Pdots surface upon cleavage of the oligonucleotide chain.

11. The electrochemiluminescence detection method of claim 10, wherein the Cas enzyme comprises Cas12 (VA type), Cas13 (VI type), and/or Cas14 (VF type).

12. The electrochemiluminescence detection method of claim 11, wherein the Cas enzyme comprises Cas12a, Cas13a, Cas13b, Cas14a, Cas14b, and/or Cas14c.

13. The electrochemiluminescence detection method of claim 10, wherein the oligonucleotide chain comprises a hairpin structure.

14. The electrochemiluminescence detection method of claim 10, wherein an EXO III enzyme is further used at the performing enzyme reaction.

15. A kit for electrochemiluminescence detection, the kit comprising:

an enzyme reaction solution comprising a Cas enzyme catalytic system comprising a guide nucleic acid capable of being bound to a target nucleic acid; and a detection chip comprising an electrochemiluminescence nanoprobe fixed on a working electrode, wherein the electrochemiluminescence nanoprobe is a Pdots nanoparticle, into which a conjugated polymer and a copolymer molecule are polymerized, wherein the Pdots nanoparticle is modified with an oligonucleotide chain modified with a quencher molecule, and wherein the oligonucleotide chain comprises a single-stranded terminal portion that can be cleaved by Cas enzymes activated by a target nucleic acid and a double-stranded portion that can be cleaved by DNA exonucleases.

16. The kit of claim 15, wherein the enzyme reaction solution further contains an EXO III enzyme.

17. The kit of claim 15, wherein the detection chip is a disposable Pdots disposable detection chip with a screen-printed three-electrode sheet used as the working electrode.

18. The production method of claim 1, wherein the conjugated polymer comprises PDHF:

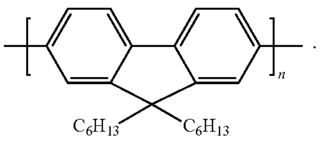

PDHF

19. The production method of claim 1, wherein the conjugated polymer comprises PFO:

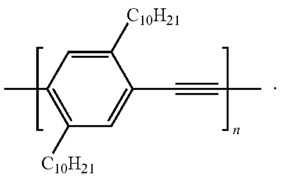

PPE

20. The production method of claim 1, wherein the conjugated polymer comprises PPE:

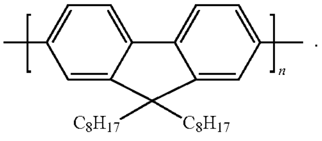

PFO

* * * * *

SEQUENCE LISTING

```
Sequence total quantity: 7
SEQ ID NO: 1           moltype = DNA  length = 39
FEATURE                Location/Qualifiers
source                 1..39
                       mol_type = genomic DNA
                       organism = human papillomavirus
SEQUENCE: 1
aatatgtcat tatgtgctgc catatctact tcagaaact                        39

SEQ ID NO: 2           moltype = DNA  length = 39
FEATURE                Location/Qualifiers
source                 1..39
                       mol_type = genomic DNA
                       organism = human papillomavirus
SEQUENCE: 2
agtttctgaa gtagatatgg cagcacataa tgacatatt                        39

SEQ ID NO: 3           moltype = DNA  length = 11
FEATURE                Location/Qualifiers
source                 1..11
                       mol_type = other DNA
                       organism = synthetic construct
SEQUENCE: 3
tttttatttt t                                                      11

SEQ ID NO: 4           moltype = DNA  length = 45
FEATURE                Location/Qualifiers
source                 1..45
                       mol_type = other DNA
                       organism = synthetic construct
SEQUENCE: 4
ttttttttta ccattttttt aacttatttg gttcagcgtt ccttt                45

SEQ ID NO: 5           moltype = RNA  length = 41
FEATURE                Location/Qualifiers
source                 1..41
                       mol_type = other RNA
                       organism = synthetic construct
SEQUENCE: 5
taatttctac taagtgtaga ttgaagtaga tatggcagca c                    41

SEQ ID NO: 6           moltype = DNA  length = 23
FEATURE                Location/Qualifiers
source                 1..23
                       mol_type = other DNA
                       organism = synthetic construct
SEQUENCE: 6
tttttagcaa cctcaaactt att                                         23

SEQ ID NO: 7           moltype = DNA  length = 18
FEATURE                Location/Qualifiers
source                 1..18
                       mol_type = other DNA
                       organism = synthetic construct
SEQUENCE: 7
gtttgaggtt gctaaaaa                                               18
```